United States Patent [19]

van der Stelt

[11] 4,228,287
[45] Oct. 14, 1980

[54] PIPERIDINEMETHYL ETHERS

[75] Inventor: Cornelis van der Stelt, Haarlem, Netherlands

[73] Assignee: N.V. Koninklijke Pharmaceutische Fabrieken, Meppel, Netherlands

[21] Appl. No.: 166,641

[22] Filed: Jul. 27, 1971

[30] Foreign Application Priority Data

Aug. 5, 1970 [GB] United Kingdom ............... 37746/70

[51] Int. Cl.³ ............................................ C07D 211/22
[52] U.S. Cl. ..................................... 546/236; 424/267
[58] Field of Search ...................... 260/293.83; 54/236

[56] References Cited

U.S. PATENT DOCUMENTS

| | | |
|---|---|---|
| 2,508,422 | 5/1950 | Rieveschl . |
| 2,567,351 | 9/1951 | Rieveschl .......................... 260/247.7 |
| 2,708,194 | 5/1955 | Blicke . |
| 2,751,388 | 6/1956 | Levy ................................. 260/294.7 |
| 3,097,212 | 7/1963 | Jucker et al. |

OTHER PUBLICATIONS

Ariens, *Molecular Biology*, vol. I, pp. 204–205, Academic Press, N.Y., London, (1964).
Ehrhart/Ruschig, *Arzneimittel*, 2nd Ed, Verlag Chemie, Weinheim (1972) Band 1, pp. 302–319.
Handbuch der Esperimentellen Pharmakologie, vol. XVIII/2, pp. 175–177, Ed. Mauricio Roacha e Silva, Springer Verlag (1978).
J. M. van Rossum, *Arch. Int. Pharacodyn, Ther*, vol. 143, pp. 299–330 (1963).
Burger, "Medicinal Chemistry", 2nd Ed. Interscience Publishers, New York, pp. 525, 532 and 533 (1960).
Loew et al., *J. Pharmacol. Exp. Therapeut.*, vol. 83, pp. 120–129 (1946).
Nauta et al., Proceedings of the 3rd International Pharmacological Meeting, Jul. 24–30, 1966, reprinted in *Physico-Chemical Aspects of Drug Actions*, Pergamon Press, N.Y. pp. 305–325 (1968).
Antonsen, *Acta Pharmacol. et Toxicol.* vol. 26, sup. 2, pp. 1–60 (1968).
Antonsen, *Acta Pharmacol. et toxicol.*, vol. 25, pp. 405–419 (1967).
Burger, "Medicinal Chemistry", 3rd Ed. Interscience Publishers, N.Y. pp. 1648–1659 (1970).
Ariens, *Drug Design*, vol. VI, Academic Press, pp. 34–40 (1975).
Jent et al., *Experientia*, vol. 32, p. 757 (1976).
Ringdoc Citation, 431R, abstract of Gamburgan et al., *Khim.-Farmatsevt. Zh.*, vol. 10, No. 8, pp. 60–66 (1976).
Goodman & Gilman, "The Pharmacological Basis of Therapeutics," 4th Ed., pp. 640–641.

Primary Examiner—John M. Ford
Attorney, Agent, or Firm—Robert E. Burns; Emmanuel J. Lobato; Bruce L. Adams

[57] ABSTRACT

A tertiary base of the formula:

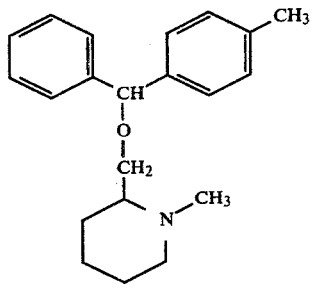

and its acid addition and quaternary ammonium salts is described. The compounds exhibit strong antihistaminic activity in animals. There is also described and claimed a method for their preparation and use as therapeutic agents in the form of therapeutic compositions.

2 Claims, No Drawings

PIPERIDINEMETHYL ETHERS

BRIEF DESCRIPTION OF THE INVENTION

There are provided accordingly new therapeutically useful piperidine derivatives, a process for their preparation and pharmaceutical compositions containing them. The new compounds of the invention are 1-methyl-2-[[(p-methyl-a-phenylbenzyl)oxy]methyl]piperidine of the formula:

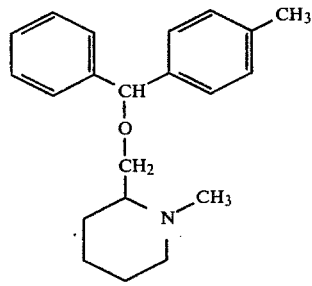

and it acid addition and quaternary ammonium salts.

The ether of formula I and its salts have valuable therapeutic properties. Their antihistaminic activity is of the same order as the activity of N,N-dimethyl-2-[(p-methyl-a-phenylbenzyl)oxy]ethylamine. Especially preferred are the quaternary ammonium salts formed with alkyl halides, and particularly 1,1-dimethyl-2-[[(p-methyl-a-phenylbenzyl)oxy]methyl]piperidinium bromide which compound shows a very high antihistaminic activity with a minimum of side effects. Quaternization of tertiary bases with an antihistamine activity tends to lower the activity as shown, for instance, by Loew et al. (J. Pharmacol., 86, 229–237 (1946)). The anticholinergic activity of tertiary bases is generally increased by quaternization (S. Antonsen, Acta pharmacol. toxicol. 26, suppl. 2 (1968)). Most surprisingly the said quaternary ammonium salts of the compound of formula I are as strong antihistaminics and weak anticholinergics as the tertiary base and its acid addition salts. They have only a weak anticholinergic activity as can be concluded from the absence of oxotremorine antagonism in the tertiary compounds and of mydriasis in both the tertiary and quaternary compounds when administered to test animals. (Oxotremorine antagonism is neither found in the quaternary compounds, but this can be ascribed to the compounds not reaching the brain region.) so undesired side effects due to anticholinergic activity are absent. The quaternary ammonium salts are preferred over the tertiary base and acid addition salts thereof as they are not able to pass the blood-brain barrier and consequently cannot affect the central nervous system. In a comparative experiment the effect of quaternization on a compound according to this invention, 1-methyl-2-[[(p-methyl-a-phenylbenzyl)oxy]methyl]-piperidine maleate and on the structurally very closely related compound 2-[(diphenylmethoxy)methyl]-1-methylpiperidine, known from the U.S. Pat. No. 2,708,194 (tested as the fumarate) has been investigated.

The antihistaminic activities were determined according to Ariëns (E. J. Ariëns (ed.) Molecular Pharmacology, Academic Press, New York, London (1964) on the isolated ileum on the guinea-pig with histamine as the agonist. The anticholinergic activities were determined according to Ariëns on the isolated rat jejunum using furtrethornium as the agonist.

The pA2 values are listed in the following table, in which:

A = 2-[(Diphenylmethoxy)methyl]-1-methylpiperidine fumarate;
B = 2-[(Diphenylmethoxy)methyl]-1-ethyl-1-methylpiperidinium iodine;
C = 1-Methyl-2-[[(p-methyl-a-phenylbenzyl)oxy]methyl]piperidine maleate;
D = 1,1-Dimethyl-2-[[(p-methyl-a-phenylbenzyl)oxy]methyl]piperidinium bromide.

| COMPOUND | ANTI-CHLORINERGIC ACTIVITY pA2 | ANTIHISTAMINIC ACTIVITY pA2 |
|---|---|---|
| A | 7.4 | 7.9 |
| B | 8.0 | 8.1 |
| C | 7.3 | 8.9 |
| D | 7.2 | 8.9 |

The table shows that in the prior art compound (A) the anticholinergic activity is considerably increased and the antihistaminic activity is not appreciably affected by quaternization (compound B). In the compounds of the invention (C and D) quaternization has no significant influence on both activities.

The base of formula I and its non-toxic acid addition and quaternary ammonium salts may be used as therapeutics. Suitable acid addition salts containing pharmaceutically acceptable non-toxic anions are, for example, the hydrohalides, sulphates, oxalates, tartrates, fumarates, acetates, citrates, maleates, succinates, lactates and pamoates.

According to a feature of the invention, the piperidine derivative of formula I is prepared by reacting a diphenylmethyl compound of the formula:

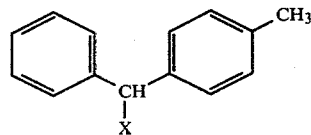

with a piperidine compound of the formula:

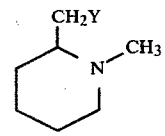

in which formula X and Y represent hydroxyl groups, or X represents a halogen atom and Y represents a hydroxyl group or X represents a group OM (wherein M represents an alkali metal atom) and Y represents a halogen atom. The reaction is preferably performed by heating the reactants in an inert organic solvent, for example benzene, toluene or xylene.

When X and Y both are hydroxyl groups, the reaction is preferably carried out in the presence of an acid that is not volatile at the reaction temperature, e.g. toluene-p-sulphonic acid, and under reduced pressure. When X is a halogen atom and Y is a hydroxyl group, it is preferred to employ an excess of the piperidine compound to bind the acid formed during the reaction. The reaction may also be carried out by heating equimolar quantities of both reactants in the presence of a basic condensation agent, such as sodium or a tertiary amine (e.g. triethylamine).

The starting materials of formula II or III wherein X or Y is a halogen atom or a group OM may be prepared from the corresponding alcohols in manner known per se. The halides may, for example, be obtained by reaction of the alcohol with a thionyl halide. The conversion of the diphenylmethanol into an alkali metal derivative may, for example, be effected by reaction with an alkali metal or an alkali metal hydride, dissolved or suspended in an inert organic solvent (e.g. benzene or toluene) or with an alkali metal alkoxide (e.g. sodium ethoxide) which is dissolved in an alcohol such as ethanol.

Due to the presence of two asymmetric carbon atoms in the ether of formula I the products are obtained as mixtures of diastereoisomers with no sharp melting point.

Acid addition and quaternary ammonium salts of the ether of formula I may be prepared by methods known per se. For example, the base may be treated with the equivalent amount of the acid in an inert solvent to obtain the corresponding acid addition salt, or the base may be treated with the equivalent amount of an appropriate alkyl halide or dialkylsulphate in a solvent having high dielectric properties, for example acetonitrile, to obtain the quaternary ammonium salt. By the term "methods known per se" as used in the specification is meant methods heretofore used or described in the literature.

The following Examples illustrate the invention:

EXAMPLE I (a) A solution of 86.6 g (0.4 mole) of p-methyl-a-phenylbenzylchloride in 500 ml of anhydrous xylene is added dropwise to 103.2 g (0.8 mole) of 1-methylpiperidin-2-ylmethanol. After 4 hours refluxing, (1-methylpiperid-2-yl)methanol hydrochloride is filtered off and the xylene solution is washed three times with water, dried over sodium sulphate and concentrated by evaporation of solvent. The residue is dissolved in diethyl ether and an ethereal solution of maleic acid is added. The precipitate is filtered off. It consists of 40 g of 1-methyl-2-[[(p-methyl-a-phenylbenzyl)oxy]methyl]-piperidine maleate. The product is crystallised twice from a mixture of acetone, ethanol and diethyl ether. Melting point 127°–145° C. Yield 50%.

Analysis: Calculated for $C_{25}H_{31}NO_5$: 70.57% C; 7.34%H; 3.29%N Found: 70.4%C; 7.3%H; 3.2%N (b) To a solution of 6.18 g (0.02 mole) of 1-methyl-2-[(p-methyl-a-phenylbenzyl)oxymethyl]piperidine (obtained from the maleate by addition of a 2 N sodium hydroxide solution, extraction with diethyl ether and distillation) in diethyl ether 5.64 g (0.04 mole) of methyl iodide in diethyl ether are added. After standing for 24 hours, the precipitate is filtered off and twice crystallised from a mixture of acetone and diethyl ether. 5.8 g of 1,1-dimethyl-2-[[(p-methyl-a-phenylbenzyl)oxy]methyl]piperidinium iodide are obtained. Yield 65%. Melting point: 125.5°–137.5° C.

Analysis: Calculated for $C_{22}H_{30}NOI$: 58.54%C; 6.70%H; 3.11%N Found: 58.5%C; 6.75%H; 3.0%N (c) To a solution of 33 g (0.1 mole) of 1-methyl-2-[(p-methyl-a-phenylbenzyl)oxymethyl]piperidine (obtained as described under (b) in diethyl ether 140 ml of ethyl iodide are added. After standing ten days the oily precipitate is filtered off and crystallised from a mixture of acetone, ethanol and diethyl ether and subsequently from ethanol. 1-Ethyl-1-methyl-2-[[(p-methyl-a-phenylbenzyl)oxy]methyl]piperidinium iodide is obtained. Melting point 189°–194° C.

EXAMPLE II 285 g (2.2 mole) of 1-methylpiperidin-2-ylmethanol in 1.25 liters of anhydrous xylene are added drop-wise under reflux to a solution of 216.5 g (1 mole) of p-methyl-a-phenylbenzyl chloride dissolved in 1.25 liters of anhydrous xylene. When the addition is completed, the mixture is refluxed for another 4 hours. The precipitate consisting of 1-methylpiperidin-2-ylmethanol hydrochloride is filtered off. The filtrate is washed with water until it is neutral and dried with sodium sulphate. The xylene is distilled off and the residue is dissolved in a mixture of 500 ml of ethanol and 2 liters of diethyl ether. 100 g of maleic acid, dissolved in 250 ml of ethanol, are added under stirring. The precipitate, consisting of 1-methyl-2-[(p-methyl-a-phenylbenzyl)oxymethyl]piperidine maleate is filtered off and digested in acetone. The salt is filtered off again and dissolved in water. The solution is made alkaline with 2 N sodium hydroxide and extracted with diethyl ether. The extract is dried over sodium sulphate and the ether is evaporated. The residue, consisting of 83 g of the base, is dissolved in 900 ml of acetone and then methyl bromide is introduced with stirring at room temperature until no further precipitation takes place. 1800 ml of petroleum ether (boiling range 40°–60° C.) are added to effect complete precipitation of the methobromide formed. The precipitate is filtered off and dried over sodium sulphate. To remove p-methyl-a-phenyl-benzylalcohol, present as a contaminant, the product is refluxed for 6 hours in 1000 ml of toluene. Filtration yields 90 g of 1,1-dimethyl-2[[(p-methyl-a-phenylbenzyl)oxy]methyl]piperidinium bromide. Melting point 180.2°–180.9° C.

The invention includes within its scope pharmaceutical compositions containing, as the active ingredient, the therapeutically active piperidine derivative of formula I, or nontoxic acid addition or quaternary ammonium salt thereof. The preferred types of composition are those suitable for oral administration and especially tablets, including sustained release tablets, pills and capsules including the substance. The tablets and pills may be formulated in the usual manner with one or more pharmaceutically-acceptable diluents or excipients, for example lactose, starch, calcium sulphate, dicalcium phosphate, microcrystalline cellulose or formaldehyde-casein, and include disintegration agents, for example amylum, sodium alginate, aerosil, Esma-Spreng (methylene casein) dioctyl sodium sulphosuccinate or potassium bicarbonate, and include materials of a lubricating nature, for example calcium or magnesium stearate, Precirol (a mixture of glycerol palmitate and stearate), stearic acid, talcum or polyethylene glycol, and include binding agents, for example gelatin, polyvinylpyrrolidone, or cellulose derivatives such as methyl cellulose. Capsules made of absorbable material, such as gelatin, may contain the active substance alone or in admixture with a solid or liquid diluent. Liquid preparations may be in the form of suspensions, emulsions, syrups or elixirs of the active substance in a liquid medium commonly used for making orally acce  
pharmaceutical formulations, such as vegetable o   , for example olive oil, arachis oil or sesame oil, polysorbates, propylene glycol, polyethylene glycol, glycerol or a syrup of elixer base.

The active substance may also be made up in a form suitable for parenteral administration, i.e. as a suspension or emulsion in an organic liquid usually employed for injectable preparations, for example a vegetable oil such as olive oil. The active substance can also be used in the form of preparations for local application such as salves, ointments, lotions or powders, containing generally used excipients. Ointments may, for instance, contain semi-solid ointment bases such as vaseline. In powders the active substance may be mixed with finely divided solid substances such as talc or boric acid.

The dosage and method of administration will depend on the mammalian species and the disease treated. In adult humans the oral dosage will be from 25 to 250 mg, preferably treatment of skin diseases, preparations such as salves, ointment, lotions or powders containing from 0.1 to 5%, preferably 1 to 2%, by weight of the active substance may be used.

The following Example illustrates a pharmaceutical preparation according to the invention.

EXAMPLE III 50 g of 1,1-dimethyl-2-[[(p-methyl-a-phenylbenzyl)oxy]methyl]piperidinium bromide,
33 g of saccharis lactis,
87 g of amylum and
10 g of polyvinylpyrrolidone are mixed and granulated with ethanol. The granulate is dried and mixed with 14 g of amylum and 6 g of a mixture of 8 parts of talcum, 1 part of aerosil and 1 part of magnesium stearate. The mixture is then compressed into tablets of 200 mg, each containing 50 mg of the active substance.

What is claimed is:

1. A non-toxic quaternary ammonium salt of 1-methyl-2-[[(p-methyl-α-phenyl-benzyl)oxy]methyl]piperidine of the formula

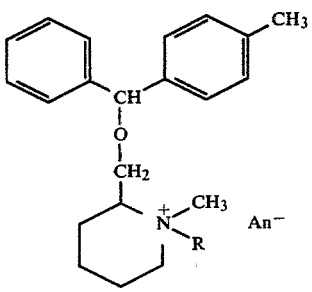

in which R represents a methyl group and an-a halogen or sulfate anion.

2. The compound according to claim 1, 1,1-dimethyl-2-[[(p-methyl-α-phenylbenzyl)oxy]methyl]piperidinium bromide.

* * * * *